(12) United States Patent
Watanabe (10) Patent No.: US 9,006,687 B2
(45) Date of Patent: Apr. 14, 2015

(54) OPTICAL UNIT, FLUORESCENCE DETECTION DEVICE, AND FLUORESCENCE DETECTION METHOD

(71) Applicant: Sharp Kabushiki Kaisha, Osaka-shi, Osaka (JP)

(72) Inventor: Yukio Watanabe, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 0 days.

(21) Appl. No.: 14/378,674

(22) PCT Filed: Feb. 20, 2013

(86) PCT No.: PCT/JP2013/054144
§ 371 (c)(1),
(2) Date: Aug. 14, 2014

(87) PCT Pub. No.: WO2013/140924
PCT Pub. Date: Sep. 26, 2013

(65) Prior Publication Data
US 2015/0028226 A1    Jan. 29, 2015

(30) Foreign Application Priority Data

Mar. 21, 2012  (JP) ................................. 2012-063445

(51) Int. Cl.
*G01N 21/64* (2006.01)
*G02B 13/18* (2006.01)
*G02B 21/00* (2006.01)

(52) U.S. Cl.
CPC .......... *G01N 21/645* (2013.01); *G02B 21/0076* (2013.01); *G01N 21/6486* (2013.01); *G01N 2021/6471* (2013.01); *G01N 2021/6478* (2013.01); *G01N 2201/105* (2013.01); *G01N 2201/06113* (2013.01)

(58) Field of Classification Search
CPC .... G01N 21/64; G02B 13/18; G02B 19/0028; G02B 3/00
USPC .............................. 250/458.1, 459.1; 359/362
See application file for complete search history.

(56) References Cited

FOREIGN PATENT DOCUMENTS

| JP | 10-003134 A | 1/1998 |
|---|---|---|
| JP | 2000-162126 A | 6/2000 |

OTHER PUBLICATIONS

Official Communication issued in International Patent Application No. PCT/JP2013/054144, mailed on May 21, 2013.

*Primary Examiner* — Mark R Gaworecki
(74) *Attorney, Agent, or Firm* — Keating & Bennett, LLP (57) ABSTRACT

A first lens configured to convert light from the objective lens into parallel light includes a concave lens part having a concave curved face in a center portion of a flat face, and a convex lens part having a convex curved face around a flat face. Further, the first lens includes first and second regions configured to diverge light through the flat face and the concave curved face and a third region configured to collect light through the convex curved face and the concave curved face. When the sample is on a sample table and sealed in a two-dimensional electrophoresis substrate, light totally reflected by a side surface of the objective lens enters the second region. In contrast, when the sample is directly on the sample table, the light enters the third region.

8 Claims, 9 Drawing Sheets

OPTICAL UNIT, FLUORESCENCE DETECTION DEVICE, AND FLUORESCENCE DETECTION METHOD

TECHNICAL FIELD

The present invention relates to an optical unit, a fluorescence detection device including the optical unit, and a fluorescence detection method using the optical unit.

BACKGROUND ART

A fluorescence detection system utilizing fluorochrome as a labeling substance has hitherto been widely used in the fields of biochemistry and molecular biology. The use of this fluorescence detection system allows evaluations, for example, analysis of genetic sequence and genetic mutation and polymorphism, and separation and identification of proteins. Thus, the fluorescence detection system is utilized for development of medicines as an example.

As the above-described evaluation method utilizing fluorescent labeling, there is often used a method in which biological compounds, such as proteins, are distributed in a gel by electrophoresis and the distribution of the biological compounds is acquired by fluorescence detection. In the electrophoresis, electrodes are set in a solution such as a buffer solution, and an electric field gradient is produced in the solution by the application of direct current. At this time, when protein, DNA (Deoxyribonucleic acid), and RNA (ribo nucleic acid) having charge exist in the solution, molecules having a positive charge are attracted to a cathode and molecules having a negative charge are attracted to an anode. Thus, biomolecules can be separated.

Two-dimensional electrophoresis serving as one evaluation method using the above-described electrophoresis is an evaluation method in which biomolecules are two-dimensionally distributed in a gel by combining two kinds of electrophoresis methods, and is considered as the most effective method for proteomic analysis.

As the electrophoresis methods to be combined, for example, two kinds of methods are mainly used, that is, "electrofocusing utilizing differences in isoelectric points among individual proteins" is used as the first dimension, and "SDS-PAGE (sodium dodecyl sulfate-polyacrylamide gel electrophoresis) for separating proteins by the molecular weight" is used as the second dimension. Fluorochrome is applied to the proteins serving as the biomolecules thus separated before or after electrophoresis.

Further, an image reading device is widely spread in the fields of biochemistry and molecular biology. In the image reading device, a gel support in which the biomolecules (proteins) produced as described above are two-dimensionally distributed is irradiated with excitation light, the intensity of generated fluorescence is acquired, and an image of a fluorescence distribution (protein distribution) is displayed on the basis of the intensity.

As a method for holding the two-dimensional distribution of the biomolecules, a method is also performed, in which the biomolecules are not only held in the gel, but also transferred from the gel to a membrane by utilizing electrophoresis or a capillary action after proteins are separated in the gel. In this case, similarly to image reading using the gel support, the fluorescence distribution on a transfer support formed by the membrane can be imaged by an image reading device.

As the above-described image reading device that reads out an image of a biomolecular distribution from a gel support or a transfer support in which biomolecules are two-dimensionally distributed, Japanese Unexamined Patent Application Publication No. 10-3134 (PTL 1) discloses an image reading device.

In the above-described conventional image reading device, a mirror having a hole in its center portion is mounted on an optical head to be moved in a main scanning direction, and laser light (excitation light) with a wavelength in accordance with the wavelength of a fluorescent substance is applied through the hole of the mirror from a light source to a transfer support on which electrophoresis of denatured DNA labeled by the fluorescent substance is recorded. Then, fluorescence emitted by excitation of fluorochrome in the transfer support is reflected around the hole of the mirror, is photoelectrically converted by a multiplier, and is then detected. In this way, one line of image data is stored in a line buffer. Subsequently, by repeating the above operations while moving the optical head in a sub-scanning direction orthogonal to the main scanning direction, a two-dimensional visible image (fluorescence image) is obtained by an image processing device.

As described above, in the conventional image reading device, excitation light is applied onto the transfer support without using a dichroic mirror. Hence, compared to a method in which excitation light is applied through the dichroic mirror, greater excitation energy can be applied to the transfer support. This can increase the S/N ratio of photoelectrically detected signals (image information).

However, to detect weak fluorescence, a further increase in the S/N ratio is required. Accordingly, Japanese Unexamined Patent Application Publication No. 2000-162126 (PTL 2) discloses an image information reading device as an optical head type image reading device that provides a higher S/N ratio of detected signals than the conventional image reading device.

In this image information reading device, a mirror having a hole in its center portion is mounted on an optical head to be moved in a main scanning direction, and laser light with a wavelength for exciting fluorochrome is applied upward through the hole of the mirror from a laser light source onto a transfer support in which biogenic substances labeled by the fluorochrome are distributed. Then, fluorescence emitted downward by excitation of the fluorochrome in the transfer support reaches the mirror. In contrast, fluorescence emitted to the upper side of the transfer support is reflected by an inner surface of a concave mirror, travels downward, passes through the transfer support, and reaches the mirror in the optical head. In this way, both the fluorescences reaching the mirror are reflected around the hole of the mirror, are photoelectrically converted by a multiplier, and are then detected. Thus, one line of image data is stored in a line buffer. By subsequently repeating the above operations while moving the optical head in a sub-scanning direction orthogonal to the main scanning direction, a two-dimensional visible image (fluorescence image) is obtained by an image processing device.

By thus increasing the amount of fluorescence to be detected by the multiplier, the S/N ratio of photoelectrically detected signals (image information) can be increased.

However, the above-described conventional image information reading device has the following problems.

That is, in synchronization with movements of the optical head in the main scanning direction and the sub-scanning direction, the concave mirror disposed above the transfer support also needs to be moved in the same directions. This complicates a moving mechanism for the concave mirror.

Further, the fluorescence is emitted from the transfer support at a wide angle. To efficiently detect the fluorescence, the fluorescence emitted at the wide angle needs to be collected at the multiplier. As a method for collecting fluorescence emitted at a wide angle with as high efficiency as possible, there is a method using an objective lens having high NA (numerical aperture). However, this increases the size of a lens element.

In this case, with the increase in size of the objective lens for collecting fluorescence, the sizes of optical elements set in the way to guide the fluorescence to the multiplier, such as a reflective mirror, a laser-light cut filter, and a light collecting lens, are also increased. For this reason, in the image reading device in which the optical system including the optical head is scanned, the total size increases with the increase in size of the optical elements. Particularly when the detection system including the multiplier is scanned while being entirely mounted on the optical head, the weight of a scanning unit increases. Hence, it is feared that high-speed scanning cannot be achieved.

Further, between a first case where a gel support in which the biomolecules (proteins) are two-dimensionally distributed or a transfer support in which a pattern of the gel support is transferred on a membrane is directly placed on a glass plate to read an image of distribution of the biomolecules and a second case where a gel support in which the biomolecules (proteins) are two-dimensionally distributed is placed on the glass plate while being sealed in a two-dimensional electrophoresis substrate to read an image of distribution of the biomolecules, the distance from the objective lens to the support having the two-dimensional distribution is different by an amount corresponding to the thickness of a portion of the two-dimensional electrophoresis substrate on a lower side of the sealed support. The distance is longer in the second case than in the first case.

Therefore, when the position in the optical axis direction of the optical system including the objective lens is set to be the most suitable for the first case, fluorescence from the gel support is not collected by the multiplier in the second case. Particularly when an objective lens having high numerical aperture NA is used, the above problem is pronounced in an outer peripheral portion of the objective lens.

CITATION LIST

Patent Literature

PTL 1: Japanese Unexamined Patent Application Publication No. 10-3134
PTL 2: Japanese Unexamined Patent Application Publication No. 2000-162126

SUMMARY OF INVENTION

Technical Problem

Accordingly, an object of the present invention is to provide an optical unit that can accurately detect the distribution of light from a measuring object even when the distance from an objective lens to the measuring object differs, a fluorescence detection device including the optical unit, and a fluorescence detection method using the optical unit.

Solution to Problem

To solve the above problems, an optical unit according to the present invention includes:
an optical lens element that collects light from a measuring object; and
a conversion lens that converts the light collected by the objective lens element into substantially parallel light.

The objective lens element includes a total reflection part that is located in a peripheral portion to collect light by total reflection on a side surface.

The conversion lens includes a plurality of regions on which the light from the total reflection part of the objective lens element is to be incident; the plurality of regions being provided in accordance with a distance between the objective lens element and the measuring object.

The conversion lens converts light from the objective lens element incident on all portions including the plurality of regions into the parallel light substantially parallel to an optical axis.

According to the above feature, the objective lens element for collecting light from the measuring object has, in its peripheral portion, the total reflection part that collects light by total reflection on the side surface. The conversion lens for converting the light collected by the objective lens element into substantially parallel light includes a plurality of regions on which the light from the total reflection part of the objective lens element is to be incident, the plurality of regions being provided in accordance with the distance between the objective lens element and the measuring object. Therefore, for example, when the measuring object is directly placed on a sample table and when the measuring object is placed on the sample table while being sealed in a substrate, totally reflected light from the total reflection part of the objective lens element, which is susceptible to the change in the distance between the objective lens element and the measuring object, enters the different regions in the conversion lens.

Even in this case, the conversion lens converts any light incident on the different regions into the parallel light substantially parallel to the optical axis.

That is, even when light having too wide an emission angle to be collected by a normal convex lens is collected by the total reflection part of the objective lens element and the distance between the objective lens element and the measuring object differs, for example, by the amount corresponding to the thickness of the substrate, parallel light substantially parallel to the optical axis is similarly emitted from the conversion lens. For this reason, a detection optical system disposed downstream of the conversion lens can be accurately operated, regardless of the change in distance between the objective lens element and the measuring object.

In the optical unit according to an embodiment, the light entering the plurality of regions of the conversion lens from the total reflection part of the objective lens element has different spread angles in accordance with the distance between the objective lens element and the measuring object.

Each of the plurality of regions of the conversion lens converts the incident light rays having the different spread angles into light whose spread angle is substantially 0 degrees.

According to this embodiment, the conversion lens converts any light incident on the different regions into light whose spread angle is substantially 0 degrees. Therefore, even when the distance between the objective lens element and the measuring object differs, light, in which not only the center ray but also all rays are nearly parallel to the optical axis in each of the regions of the conversion lens, is emitted from the regions. For this reason, the detection optical system disposed downstream of the conversion lens can be more accurately operated, regardless of the distance between the objective lens element and the measuring object.

In the optical unit according to an embodiment, in each of the plurality of regions of the conversion lens, the sum of a curvature of an incident surface and a curvature of an emission surface is a curvature to diverge the incident light when the spread angle of the incident light is an angle that represents convergence, and the sum of the curvature of the incident surface and the curvature of the emission surface is a curvature to converge the incident light when the spread angle of the incident light is an angle that represents divergence.

According to this embodiment, each of the plurality of regions of the conversion lens diverges incident light when the incident light is convergent light, whereas it converges the incident light when the incident light is divergent light. Therefore, whether the spread angle of the incident light is the angle that represents convergence or the angle that represents divergence, the incident light can be converted into light whose spread angle is substantially 0 degrees.

In the optical unit according to an embodiment, the objective lens element has a refraction part located in a center portion to collect light by refraction.

The conversion lens has, in a peripheral portion, the region on which the light is to be incident from the total reflection part of the objective lens element.

The influence of the change in the distance between the objective lens element and the measuring object on the incident position of the incident light on the conversion lens is larger in emitted light from the total reflection part in the peripheral portion than in emitted light from the refraction part in the center portion of the objective lens element.

According to this embodiment, the region of the conversion lens on which the light from the total reflection part of the objective lens element is incident is provided in the peripheral portion. Therefore, the light that is emitted from the refraction part of the objective lens element and enters the center portion of the conversion lens is converted into substantially parallel light without passing through the region. In contrast, the light that is emitted from the total reflection part of the objective lens element and enters the peripheral portion of the conversion lens is converted into substantially parallel light by the region. In this way, all emitted light from the objective lens element can be converted into substantially parallel light.

In the optical unit according to an embodiment, the total reflection part of the objective lens element has a concentric shape with the optical axis.

The plurality of regions of the conversion lens have concentric shapes with the optical axis.

According to this embodiment, when a light source on the measuring object is a point light source, emitted light from the total reflection part of the objective lens element can be more accurately converted into substantially parallel light.

In the optical unit according to an embodiment, the measuring object is placed on a sample table having a light transmissive property.

The objective lens element and the conversion lens are disposed opposed to a surface of the sample table opposite from a surface on which the measuring object is placed.

The objective lens element collects the light emitted from the measuring object via the sample table.

According to this embodiment, the measuring object is placed on the sample table having the light transmissive property, and the objective lens element collects the light from the measuring object via the sample table. Hence, for example, the distance between the objective lens element and the measuring object differs between the case where the measuring object is directly placed on the sample table and the case where the measuring object is placed on the sample table while being sealed in the substrate. Even in this situation, parallel light substantially parallel to the optical axis is similarly emitted from the conversion lens. For this reason, the detection optical system downstream of the conversion lens can be accurately operated, regardless of the change in distance between the objective lens element and the measuring object.

A fluorescence detection device according to the present invention includes:

a light source unit that irradiates a measuring object with excitation light that excites fluorescence;

the optical unit of the present invention on which the fluorescence emitted from the measuring object by the irradiation of the excitation light is to be incident, the optical unit converting the incident fluorescence into substantially parallel fluorescence;

a wavelength filter on which the substantially parallel fluorescence from the optical unit is to be incident, the wavelength filter reducing a light component with a wavelength equal to a wavelength of the excitation light; and a photodetection element that detects the fluorescence from the wavelength filter.

The objective lens element in the optical unit has, in a center portion, an excitation-light transmitting part that transmits the excitation light from the light source unit, irradiates the measuring object with the excitation light from the light source unit via the excitation-light transmitting part, and collects the fluorescence from the measuring object.

According to the above feature, there is provided the optical unit of the present invention that can emit parallel light substantially parallel to the optical axis, regardless of the change in distance between the objective lens element and the measuring object. The objective lens element in the optical unit irradiates the measuring object with the excitation light from the light source unit via the excitation-light transmitting part in the center portion, and collects fluorescence emitted from the measuring object. Therefore, regardless of the change in distance between the objective lens element and the measuring object, fluorescence nearly parallel to the optical axis is emitted from the conversion lens in the optical unit and enters a wavelength filter disposed on a downstream side.

As a result, stray light having a wavelength component equal to a wavelength of the excitation light can be accurately cut by the wavelength filter.

A fluorescence detection method according to the present invention includes:

emitting, from a light source unit, excitation light that excites fluorescence;

applying the excitation light from the light source unit to a measuring object through a center portion of the objective lens element in the optical unit of the present invention;

collecting the fluorescence emitted from the measuring object by the application of the excitation light by the objective lens element;

converting the fluorescence collected by the objective lens element into substantially parallel light by the conversion lens in the optical unit;

subtracting, by a wavelength filter, a light component having a wavelength equal to a wavelength of the excitation light from the substantially parallel fluorescence converted by the conversion lens; and detecting the fluorescence from the wavelength filter by a photodetection element.

According to the above feature, there is provided the optical unit of the present invention that can emit parallel light substantially parallel to the optical axis, regardless of the change in distance between the objective lens element and the measuring object. Excitation light from the light source unit is applied to the measuring object through the center portion of the objective lens element in the optical unit, and fluorescence emitted from the measuring object is collected by the objective lens element. Therefore, regardless of the change in distance between the objective lens element and the measuring object, fluorescence nearly parallel to the optical axis is emitted from the conversion lens in the optical unit, and enters a wavelength filter disposed on a downstream side.

As a result, stray light having a wavelength component equal to the wavelength of the excitation light can be accurately cut by the wavelength filter.

Advantageous Effects of Invention

As is clear from the above, in the optical unit of the present invention, the total reflection part for collecting light by total reflection is provided in the peripheral portion of the objective lens element, and the conversion lens includes a plurality of regions on which light from the total reflection part is to be incident. The regions are provided in accordance with the distance between the objective lens element and the measuring object. The conversion lens converts any light incident on the different regions into the parallel light substantially parallel to the optical axis. Therefore, even when light having too wide an emission angle to be collected by the normal convex lens is collected by the total reflection part of the objective lens element and the distance between the objective lens element and the measuring object differs, for example, by the amount in accordance with the thickness of a substrate in which the measuring object is sealed, parallel light substantially parallel to the optical axis can be emitted from the conversion lens. As a result, the detection optical system downstream of the conversion lens can be accurately operated, regardless of the change in distance between the objective lens element and the measuring object.

In the fluorescence detection device and the fluorescence detection method of the present invention, the optical unit of the present invention is provided to emit parallel light substantially parallel to the optical axis, regardless of the change in distance between the objective lens element and the measuring object, excitation light from the light source unit is applied to the measuring object through the center portion of the objective lens element in the optical unit, and fluorescence emitted from the measuring object is collected by the objective lens element. Therefore, regardless of the change in distance between the objective lens element and the measuring object, fluorescence nearly parallel to the optical axis is emitted from the conversion lens in the optical unit, and enters the downstream wavelength filter.

As a result, stray light having a wavelength component equal to the wavelength of the excitation light can be accurately cut by the wavelength filter.

DESCRIPTION OF EMBODIMENTS

The present invention will be described in detail below in conjunction with an illustrated embodiment.

Figure 1:
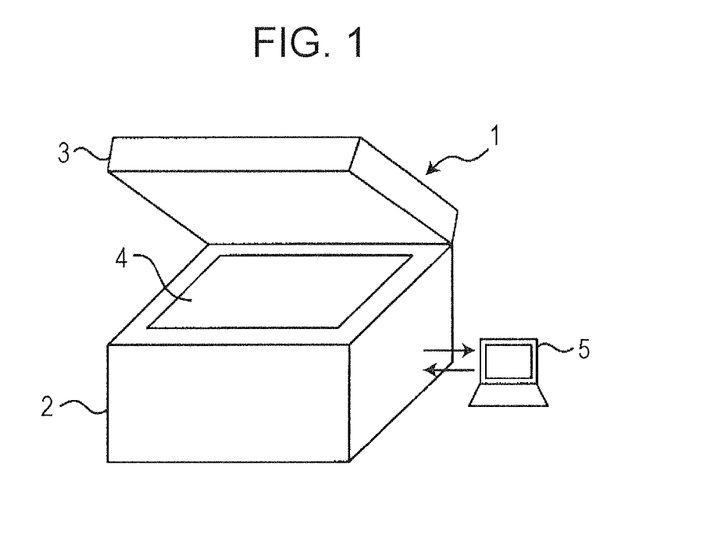
FIG. 1 is an outside view of a fluorescence detection device including an optical unit according to the present invention.

FIG. 1 is an outside view of a fluorescence detection device including an optical unit according to an embodiment. A fluorescence detection device 1 is roughly composed of a body 2 that forms a housing, and a cover 3 that covers an upper surface of the body 2. A sample table 4 made of glass is provided on the upper surface of the body 2. For example, a gel support in which biogenic substances labeled by a fluorescent substance are distributed or a transfer support, such as a membrane, (both of the supports are not illustrated) is set as a sample (measuring object) on the sample table 4.

Optical systems are disposed on a lower side of the sample table 4. Excitation light is applied to the sample set on the sample table 4 from below through the sample table 4 by an irradiation optical system, and fluorescence from the sample, which passes through the sample table 4, is detected by a detection optical system. The detection optical system is connected to an external terminal such as a PC (personal computer) 5, and for example, a measuring condition is controlled from the PC 5. Further, a fluorescence image of the sample is created by the PC 5 on the basis of detected data, and the created fluorescence image or the like is displayed on an incorporated display screen.

Figure 2:
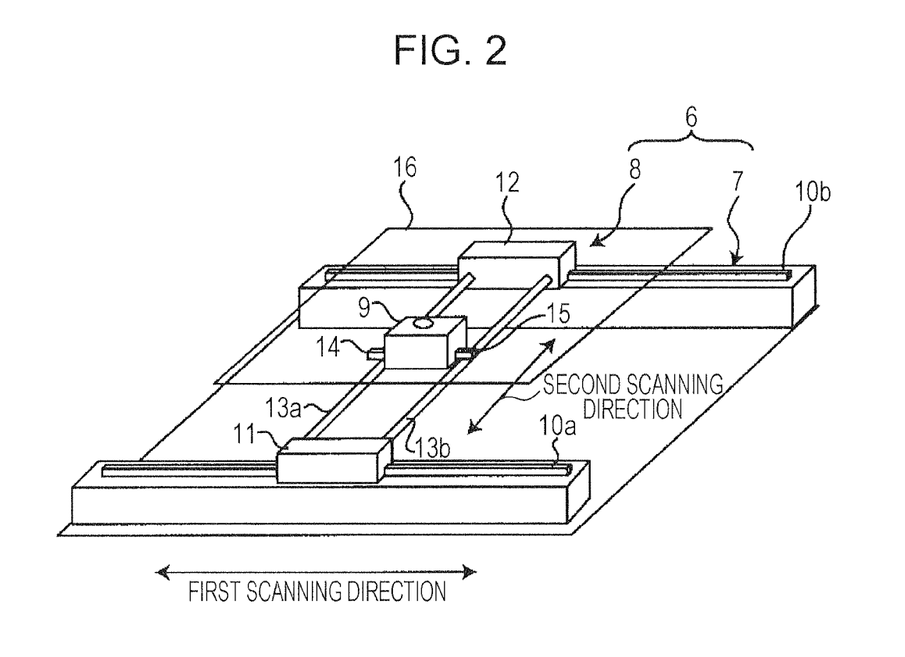
FIG. 2 is an outside view of a scanning stage installed below a sample table in FIG. 1.

FIG. 2 is an outside view of a scanning stage 6 installed below the sample table 4. This scanning stage 6 includes a first stage 7 serving as a base, and a second stage 8 disposed on the first stage 7. On the second stage 8, a scanning module 9 is disposed. The detection optical system for detecting the fluorescence is stored in the scanning module 9.

In the first stage 7 that constitutes the scanning stage 6, two guide rails 10a and 10b are disposed to extend in a first scanning direction and to be opposed to each other with a predetermined space therebetween. The second stage 8 includes a first guide member 11 that is guided by the guide rail 10a of the first stage 7 to reciprocate in the first scanning direction, and a second guide member 12 that is guided by the guide rail 10b to reciprocate in the first scanning direction.

Between the first guide member 11 and the second guide member 12 that constitute the second stage 8, two guide rails 13a and 13b are disposed to extend in a second scanning direction orthogonal to the first scanning direction and to be opposed to each other with a predetermined space therebetween. The scanning module 9 is provided with a first guide member 14 that is guided by the guide rail 13a to reciprocate in the second scanning direction, and a second guide member 15 that is guided by the guide rail 13b to reciprocate in the second scanning direction.

In a scanning method using the scanning stage 6 having the above-described structure, first, the first guide member 11 and the second guide member 12 of the second stage 8 are moved in the first scanning direction while being guided by the guide rails 10a and 10b, respectively, so as to position the second stage 8 relative to the first stage 7. After that, the first guide member 14 and the second guide member 15 of the scanning module 9 are moved in the second scanning direction while being guided by the guide rails 13a and 13b, respectively, so as to position the scanning module 9 relative to the second stage 8. Subsequently, a sample 16 is two-dimensionally scanned by repeating the above operations.

That is, in the embodiment, a moving unit in the first scanning direction is constituted by the guide rails 10a and 10b and the first and second guide members 11 and 12, and a moving unit in the second scanning direction is constituted by the guide rails 13a and 13b and the first and second guide members 14 and 15.

Although a specific description is skipped, further below the scanning stage 6 provided below the sample table 4 and in the body 2 that forms the housing, driving units, such as a motor, a driving belt, ball screws, gears, a control board, a power supply, and wires, are disposed to move the first and second guide members 11 and 12 of the second stage 8 in the first scanning direction and to move the first and second guide members 14 and 15 of the scanning module 9 in the second scanning direction.

Figure 3:
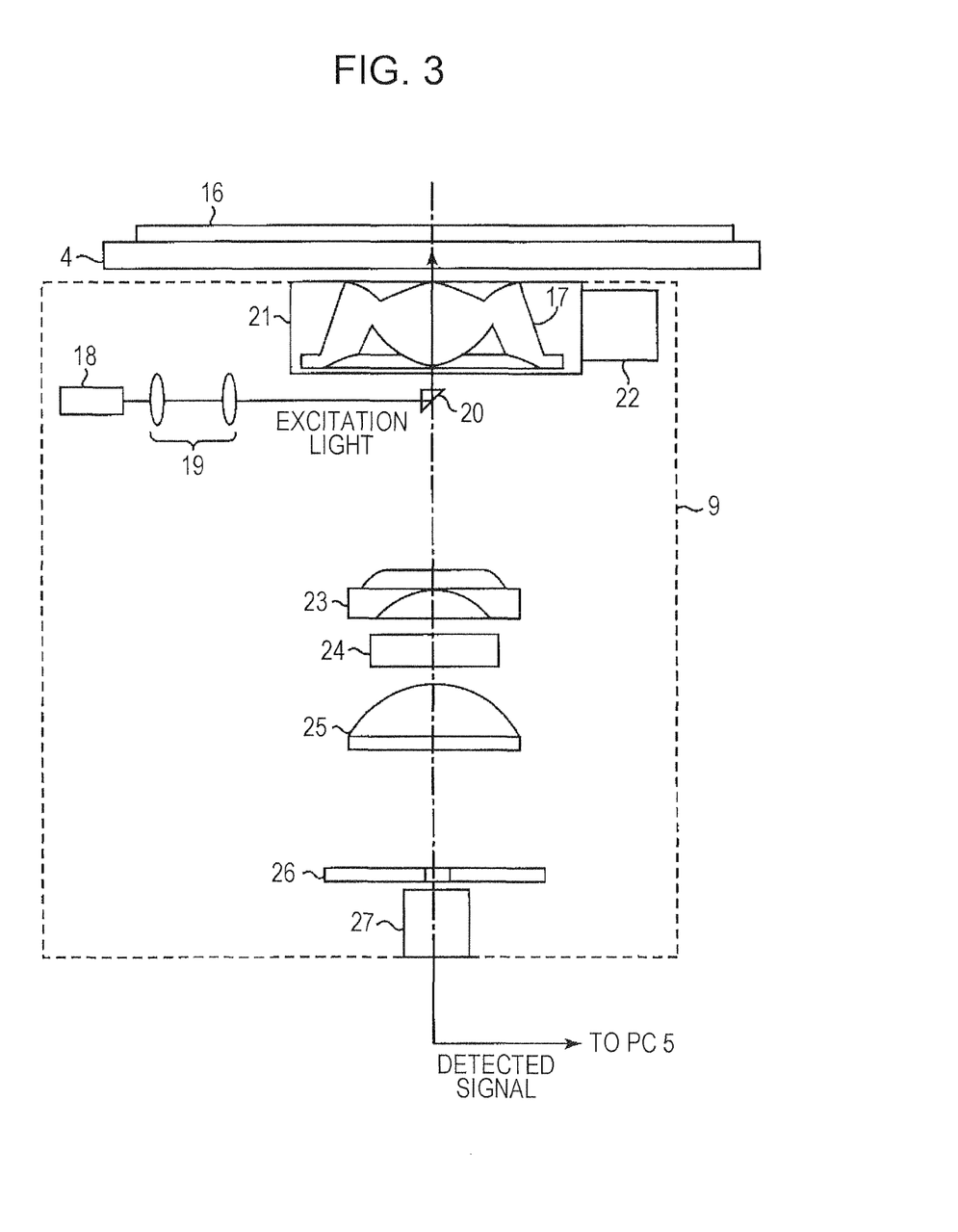
FIG. 3 is a cross-sectional view of a scanning module disposed on a second stage in FIG. 2.

FIG. 3 is a vertical sectional view illustrating a schematic structure of the scanning module 9 disposed on the second stage 8. In FIG. 3, an objective lens 17 is disposed in an upper part of the scanning module 9 and near the sample table (glass) 4 to collect fluorescence from a sample 16 set on the sample table 4. Further, a reflecting mirror 20 is disposed at a position, where the optical axis of the objective lens 17 and the optical axis of a light source 18 of excitation light intersect at right angles, to reflect excitation light, such as laser light, emitted from the light source 18 and collected by a lens unit 19 composed of a plurality of lenses so that the excitation light enters the objective lens 17.

The objective lens 17 is stored in a lens holder 21, and the lens holder 21 can be moved in the optical axis direction of the objective lens 17 by a driving unit 22 such as a stepping motor. Thus, the objective lens 17 is movable together with the lens holder 21 in the optical axis direction.

Below the reflecting mirror 20 on the optical axis of the objective lens 17, a first lens 23 for converting fluorescence from the sample 16 collected by the objective lens 17 into parallel light, a wavelength filter 24 for cutting excitation light, a second lens 25 for collecting fluorescence passing through the wavelength filter 24, and a pinhole 26 for cutting stray light of fluorescence passing through the second lens 25 are disposed in order from a side of the reflecting mirror 20. Further, below the pinhole 26 on the optical axis of the objective lens 17, a detector 27 is disposed to detect fluorescence passing through the pinhole 26.

That is, in this embodiment, the first lens 23 forms the conversion lens in the claims.

In the scanning module 9 having the above-described structure, excitation light emitted from the light source 18 is converged by the lens unit 19, is next reflected by the reflecting mirror 20, passes through the objective lens 17 and the sample table 4, and is collected at one point on a lower surface of the sample 16. In this case, the length of the reflecting mirror 20 in the longitudinal direction (direction orthogonal to the optical axis of the lens unit 19) is short, and the width thereof in a direction orthogonal to the longitudinal direction is narrow. The excitation light from the light source 18 passes only near the optical axis of the objective lens 17 (an excitation-light transmitting part).

That is, in the embodiment, the light source 18, the lens unit 19, and the reflecting mirror 20 constitute the light source unit in the claims.

The fluorescence is isotropically emitted around from a portion of the sample 16 irradiated with the excitation light. A component of the emitted fluorescence, which has passed through the sample table 4 made of glass and entered the objective lens 17, passes through the objective lens 17, the first lens 23, the wavelength filter 24, the second lens 25, and the pinhole 26, and is detected by the detector 27. Detected signals from the detector 27 are subjected to processing, for example, AD conversion by an AD converter (not illustrated) incorporated therein, and are then transmitted to the PC 5. Thus, a distribution of fluorescence intensities at measuring points on the sample 16 is recorded in, for example, an internal memory.

Here, as described above, the fluorescence that has passed through the objective lens 17 is guided as convergent light toward the second lens 23. Then, the fluorescence is refracted by the second lens 23 so as to become light substantially parallel to the optical axis. Further, the second lens 25 collects the fluorescence. The pinhole 26 is disposed to spatially cut stray light. The wavelength filter 24 for cutting excitation light is disposed in, for example, a rotary folder (not illustrated), and can be replaced with other wavelength filters in accordance with the wavelength of the excitation light.

A detailed description will be given below of the objective lens 17.

Figure 4:
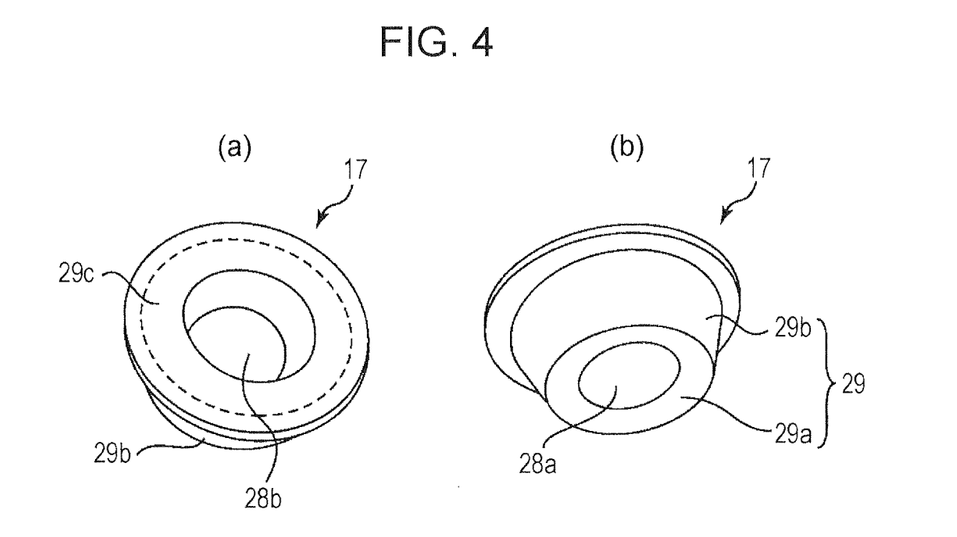
FIG. 4 includes perspective views of an Objective lens in FIG. 3.
Figure 5:
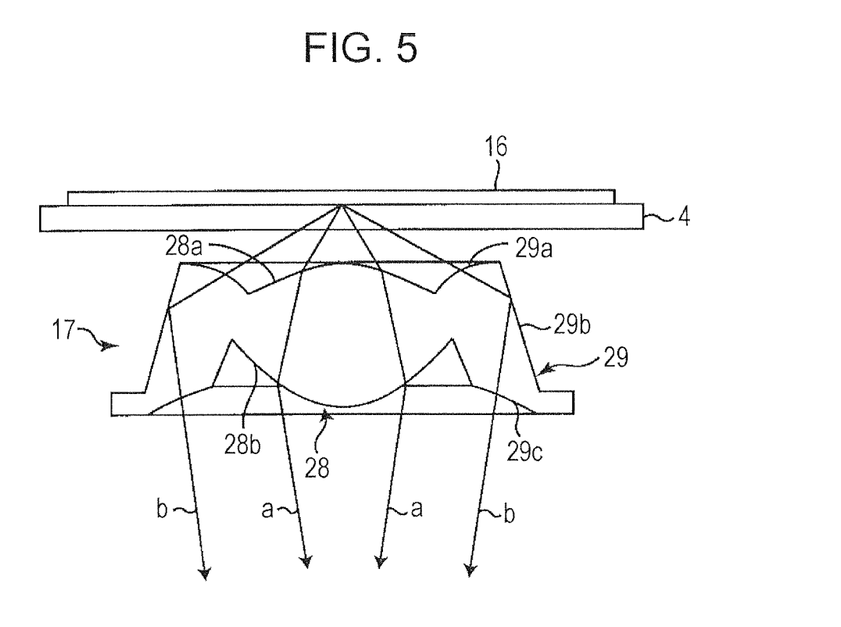
FIG. 5 is a cross-sectional view of the objective lens.

FIG. 4 includes perspective views of the objective lens 17. FIG. 4(a) is a perspective view from the reflecting mirror 20. FIG. 4(b) is a perspective view from the sample table 4. FIG. 5 is a vertical sectional view of the objective lens 17.

As can be seen from FIGS. 4 and 5, the objective lens 17 is shaped like an inverted ashtray. A center portion including the optical axis includes an upper convex surface 28a and a lower convex surface 28b that spherically project along the optical axis, and serves as a convex lens part 28 having a function of a normal convex lens (function of deflecting light only by refraction). As illustrated in FIG. 5, a fluorescence component a with a small emission angle, of fluorescence emitted from the sample 16, passes through the convex lens part 28, and is collected toward the detector 27.

A portion of the objective lens 17 around the convex lens part 27 serves as a truncated conical cylindrical body 29 opening downward. A fluorescence component b having too wide an emission angle to fit in the convex lens part 28, of the fluorescence emitted from the sample 16, enters the cylindrical body 29 from an upper end surface 29a of the cylindrical body 29, is deflected toward the optical axis by total reflection on a side surface 29b of the cylindrical body 29, and is emitted from a lower end surface 29c of the cylindrical body 29 toward the detector 27.

That is, in the embodiment, the convex lens part 28 forms the refraction part in the claims, and the cylindrical body 29 forms the total reflection part.

As described above, light having too wide an emission angle to be collected by the normal convex lens can be collected by totally reflecting, by the side surface 29b of the cylindrical body 29, a fluorescence component having too wide an emission angle to fit in the convex lens part 28, of fluorescence emitted from the sample 16. For this reason, sensitivity of the detector 27 can be increased.

The lens element itself can be made more compact than when the objective lens of this fluorescence detection device 1 is realized by a normal convex lens having an NA equal to that of the objective lens 17.

Since an interference filter having a sharp cutoff property is used as the wavelength filter 24, it is necessary to convert incident light on the wavelength filter 24 into light parallel to the optical axis. Accordingly, fluorescence collected through the objective lens 17 is caused to be incident on the wavelength filter 24 after being converted into nearly parallel light by the first lens 23. Here, the fluorescence can be converted into parallel light by the objective lens 17. In this case, however, the beam diameter of fluorescence increases, and this increases the sizes of the first lens 23 and the subsequent optical elements.

Therefore, when the above-described objective lens 17 having the convex lens part 28 in the center portion and the truncated conical cylindrical body 29 around the convex lens part 28 is used, the sizes of the optical elements, such as the first lens 23, the wavelength filter 24, and the second lens 25 can be reduced, and the size and weight of the scanning module 9 can be reduced.

Figure 6:
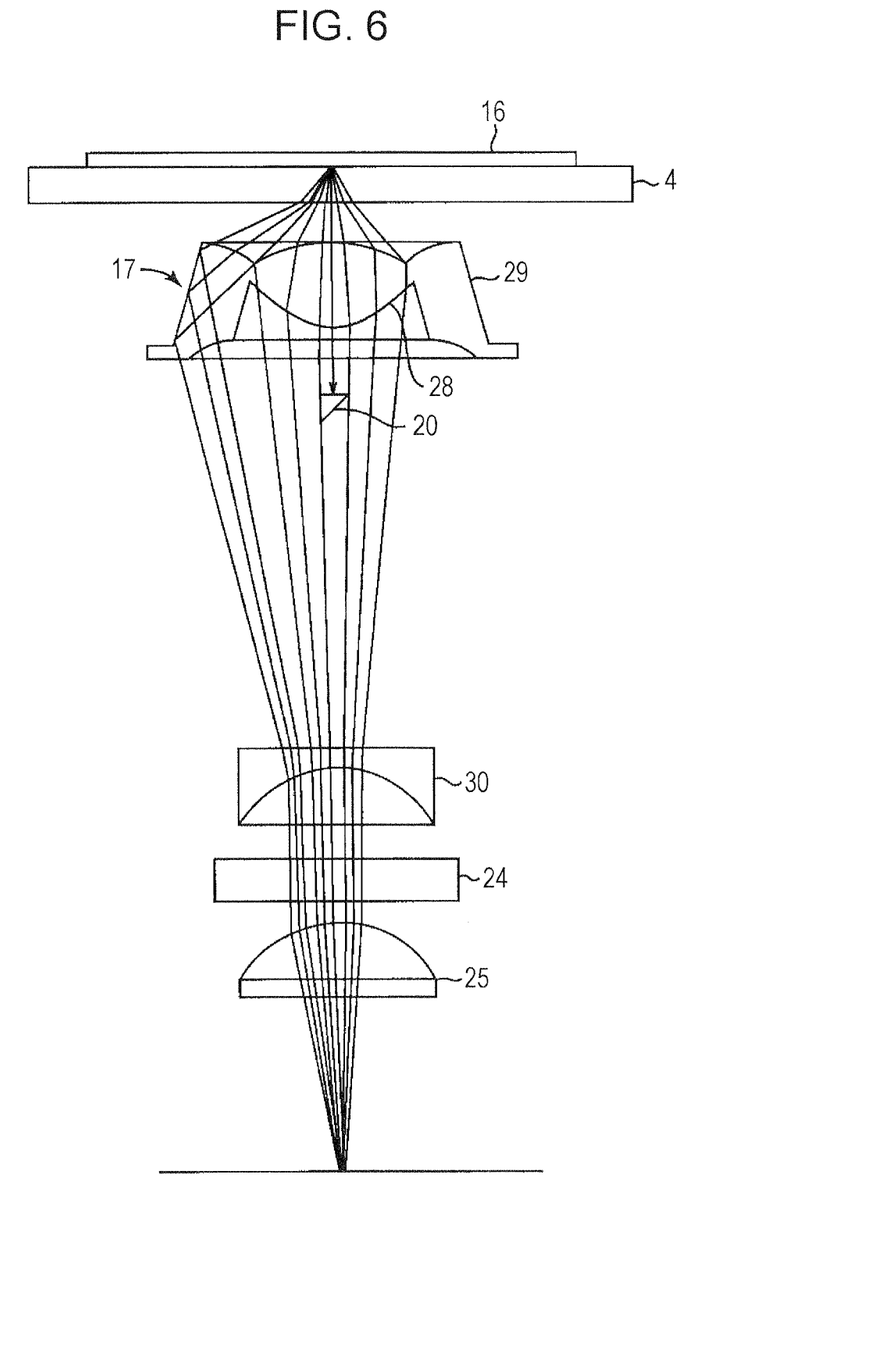
FIG. 6 is a ray diagram from the objective lens to a second lens when a first lens is replaced with a normal concave lens in FIG. 3.

When the first lens 23 for converting fluorescence collected through the objective lens 17 into a state close to parallel light and causing the fluorescence to enter the wavelength filter 24 is formed by a normal concave lens 30 having a single curved surface, a ray diagram of fluorescence emitted from the sample 16 and passing from the objective lens 17 to the second lens 25 is shown by FIG. 6. In this case, when the position of the objective lens 17 is set by the driving unit 22 such as to be focused on the position of the sample 16 (the gel support or the transfer support) directly placed on the sample table (glass) 4, the shape of the objective lens 17 is assumed to be optimized such that light passing through the convex lens part 28 of the objective lens 17 and light passing through the cylindrical body 29 are collected at almost the same position (position of the hole of the pinhole 26).

Figure 7:
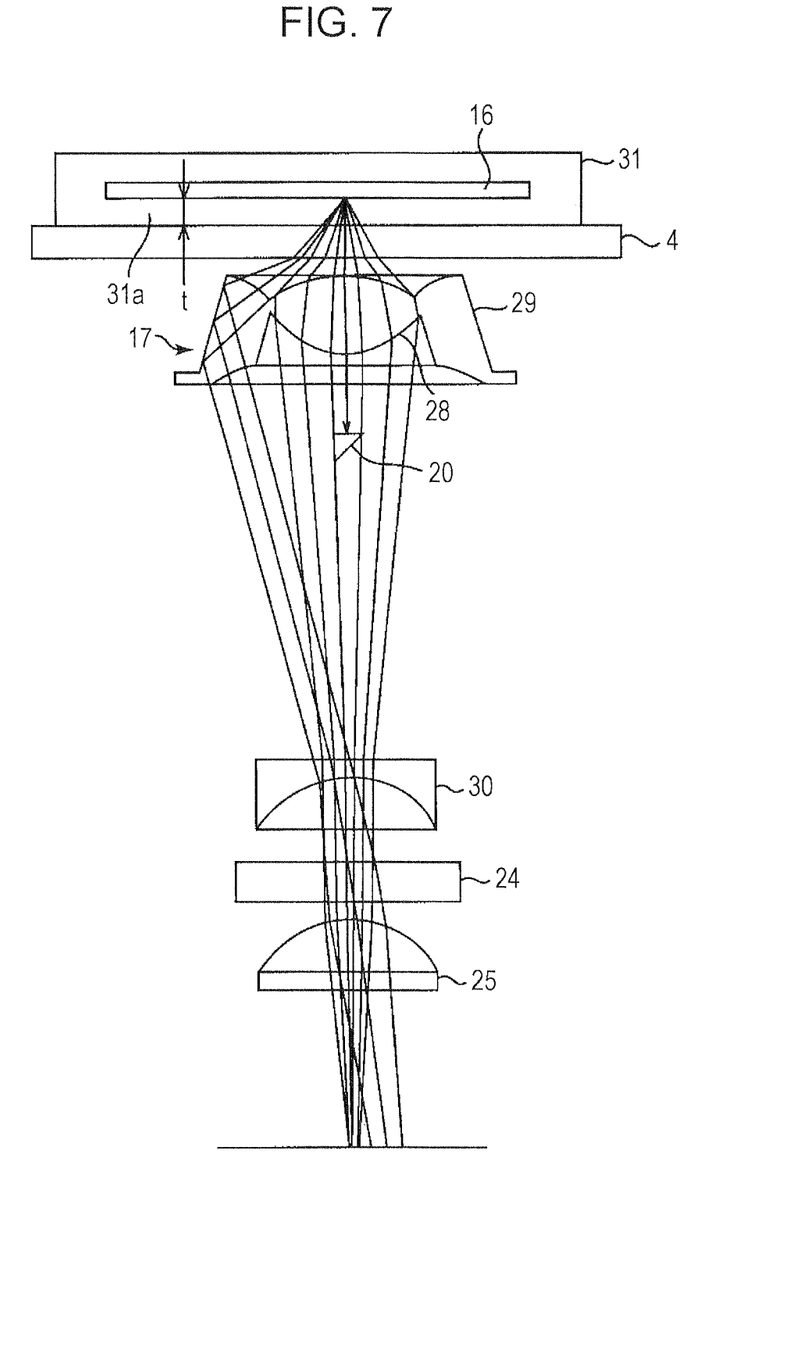
FIG. 7 is a ray diagram when a sample is sealed in a two-dimensional electrophoresis substrate in FIG. 6.

However, when the objective lens 17, whose shape is optimized as illustrated in FIG. 6, is used and fluorescence from the sample 16 is detected in a state in which the gel support serving as the sample 16 is sealed in a two-dimensional electrophoresis substrate 31 and is placed on the sample table (glass) 4, as illustrated in FIG. 7, the distance from the objective lens 17 to the sample 16 is longer by a thickness t of a lower portion 31a of the two-dimensional electrophoresis substrate 31 lower than the sample 16 than in the case illustrated in FIG. 6. Therefore, even if the position of the objective lens 17 is set such as to be focused on the position of the sample 16 sealed in the two-dimensional electrophoresis substrate 31, light passing through the convex lens part 28 of the objective lens 17 and light passing through the cylindrical body 29 are not collected at the hole of the pinhole 26. Further, the incident angle of incident light on the wavelength filter 24 is not parallel to the optical axis. This reduces stray-light cutting performance.

This is caused because the amount of aberration and the change amount of the optical path length differ between the center convex lens part 28 of the objective lens 17 and the surrounding cylindrical body 29 owing to the influence of the lower portion 31a of the two-dimensional electrophoresis substrate 31 lower than the sealed sample 16.

Accordingly, in this embodiment, the shapes of the objective lens 17 and the first lens 23 are devised as follows to address such problems.

Figure 8:
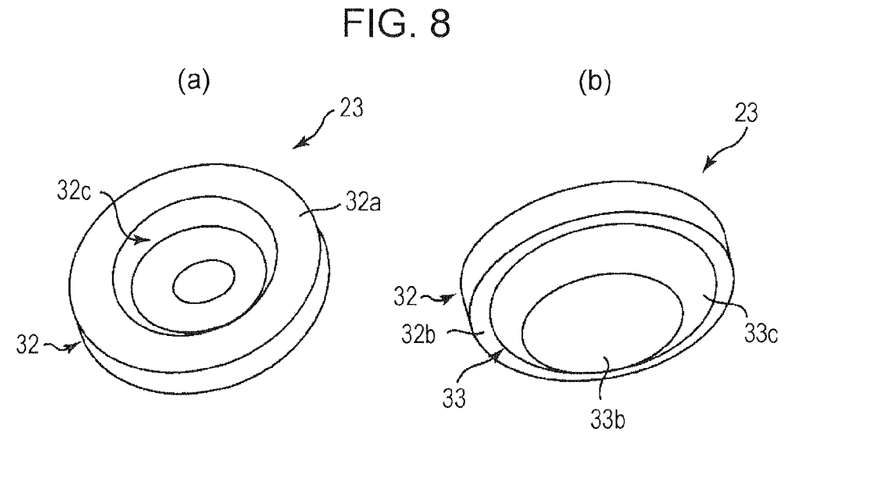
FIG. 8 includes perspective view of the first lens in FIG. 3.
Figure 9:
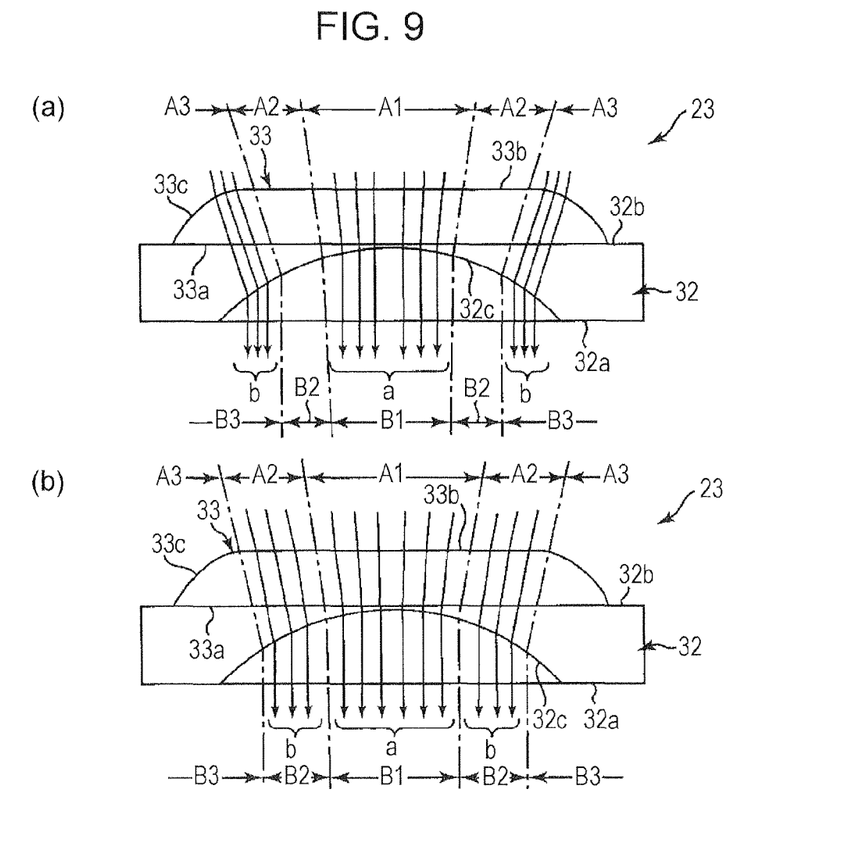
FIG. 9 includes cross-sectional views of the first lens.

FIG. 8 includes perspective views of the first lens 23. FIG. 8(a) is a perspective view from the wavelength filter 24. FIG. 8(b) is a perspective view from the reflecting mirror 20. FIG. 9 includes longitudinal sectional views of the first lens 23. FIG. 9(a) includes a ray diagram of fluorescence when the sample 16 is directly placed on the sample table 4 (hereinafter, referred to as "a first case"). FIG. 9(b) includes a ray diagram of fluorescence when the sample 16 is placed on the sample table 4 while being sealed in the two-dimensional electrophoresis substrate 31 (hereinafter referred to as "a second case").

As can be seen from FIGS. 8 and 9, the first lens 23 is configured such that a concave lens part 32, in which a flat face 32a, of two opposed flat faces 32a an 32b, has a concave curved face 32c, and a convex lens part 33, in which a convex curved face 33c is provided in an inclined portion formed only on the periphery of a flat face 33b, of two opposed flat faces 33a and 33b, are stacked while the flat face 33a of the convex lens part 33 and the flat face 32b of the concave lens part 32 are opposed to each other.

As illustrated in FIG. 9, a fluorescence component a passing through the convex lens part 28 of the objective lens 17, of fluorescence emitted from the sample 16, passes through the flat face 33b of the convex lens part 33 and the concave curved face 32c of the concave lens part 32 both in the first case and the second case.

In contrast, a fluorescence component b totally reflected by the cylindrical body 29 of the objective lens 17, of the fluorescence emitted from the sample 16, passes through the convex curved face 33c of the convex lens part 33 and the concave curved face 32c of the concave lens part 32 in the first case, as illustrated in FIG. 9(a). The fluorescence component b passes through the flat face 33b of the convex lens part 33 and the concave curved face 32c of the concave lens part 32 in the second case, as illustrated in FIG. 9(b).

The first lens 23 may be formed by simply stacking the concave lens part 32 and the convex lens part 33 in tight contact with each other, or may be formed by bonding the concave lens part 32 and the convex lens part 33. Alternatively, the concave lens part 32 and the convex lens part 33 may be formed integrally.

Figure 10:
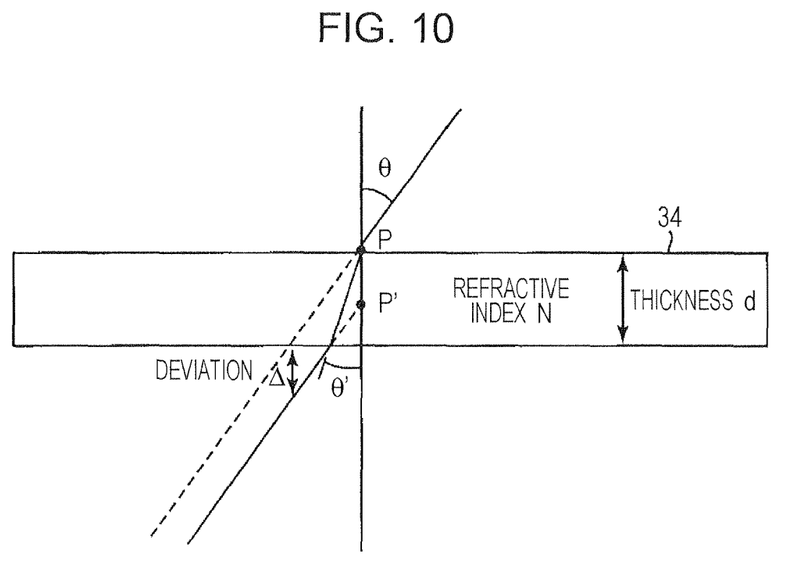
FIG. 10 explains a deviation distance Δ between a point light source and an apparent light source.

In this embodiment, the measuring object is a fluorescent portion in a spot of excitation light that is emitted from the light source 18, converged by the lens unit 19, reflected by the reflecting mirror 20, and collected at one point on the lower surface of the sample 16. Therefore, it can be considered that a point light source is adopted. In the case of a point light source, as illustrated in FIG. 10, light, which enters a light transmissive plate 34 having a refractive index N and a thickness d at an incident angle θ' from a point light source P on a front surface of the light transmissive plate 34, is refracted by a back surface of the light transmissive plate 34 and is emitted at an emission angle θ. In this case, the light emitted from the back surface of the light transmissive plate 34 appears as if it is emitted using a point P' within the light transmissive plate 34 as a light source. Between the point light source P and the apparent light source P', deviation of a distance Δ occurs. In this case, the deviation distance Δ is expressed as follows:

$$\Delta = d\{1 - (\cos\theta/N\sin\theta')\}.$$

Therefore, the deviation distance Δ increases as the thickness d of the light transmissive plate 34 increases and the incident angle θ' decreases. That is, the deviation distance Δ is longer in the second case where the sample 16 sealed in the two-dimensional electrophoresis substrate 31 is placed on the sample table 4 than in the first case where the sample 16 is directly placed on the sample table 4. Further, the deviation distance Δ is shorter in the fluorescence component b totally reflected by the cylindrical body 29 of the objective lens 17 than in the fluorescence component a passing through the convex lens part 28 of the objective lens 17. Conversely, a value (d−Δ) is larger. Here, the value (d−Δ) refers to the difference between the moving distance (=d) of the light source when the light transmissive plate 34 is provided and is not provided and the moving distance (=Δ) of the apparent light source when the light transmissive plate 34 is provided and is not provided.

Figure 11:
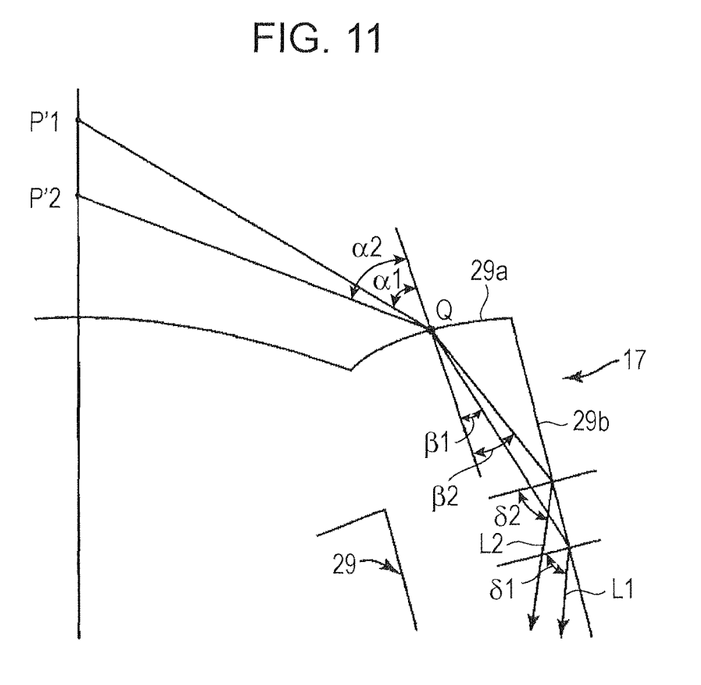
FIG. 11 illustrates the optical path of light incident from a point on an upper end face of a cylindrical body of the objective lens.

FIG. 11 illustrates the optical paths of light that enters the cylindrical body 29 from a point Q on the upper end face 29a of the cylindrical body 29 of the objective lens 17, of the fluorescence component b totally reflected by the cylindrical body 29 and having the larger value (d−Δ). Here, an optical path L1 refers to the optical path in the "first case", and an optical path L2 refers to the optical path in the "second case."

As described above, the deviation distance Δ is longer in the "second case" than in the "first case." In the "second case", the objective lens 17 is moved by the driving unit 22 toward the sample 16 in the optical axis direction by the amount corresponding to the thickness t of the lower portion 31a of the two-dimensional electrophoresis substrate 31. Hence, the influence of the deviation distance Δ on the fluorescence component a passing through the convex lens part 28 of the objective lens 17 is cancelled, but the influence on the fluorescence component b totally reflected by the cylindrical body 29 is left. In this case, an apparent light source P'1 of light incident on the point Q in the "first case" is located farther from the upper end of the objective lens 17 than an apparent light source P'2 of light incident on the point Q in the "second case." For this reason, an incident angle α and a refraction angle β at the point Q are larger (α2>α1, β2>β1) and a reflection angle δ at the side surface 29b of the cylindrical body 29 is smaller (δ2<δ1) in the "second case" than in the "first case."

As a result, as described above, when the objective lens 17, whose shape is optimized so that light passing through the cylindrical body 29 of the objective lens 17 is collected at the position of the hole of the pinhole 26 in the "first case", as illustrated in FIG. 6, is used in the "second case", the light L2 totally reflected by the side surface 29b is closer to the optical axis than the totally reflected light 21 in the "first case", as illustrated in FIG. 11. Therefore, as illustrated in FIG. 7, the incident angle of incident light on the wavelength filter 24 is not parallel to the optical axis, and the incident light is not collected at the position of the hole of the pinhole 26.

Accordingly, in this embodiment, first, the totally reflected light L2 from the side surface 29b in the "second case" is caused to be incident on the wavelength filter 24 while being parallel to the light passing through the convex lens part 28. Further, the reflected light L1 from the side surface 29b in the "first case" is also caused to be incident on the wavelength filter 24 while being parallel to the light passing through the convex lens part 28.

Figure 12:
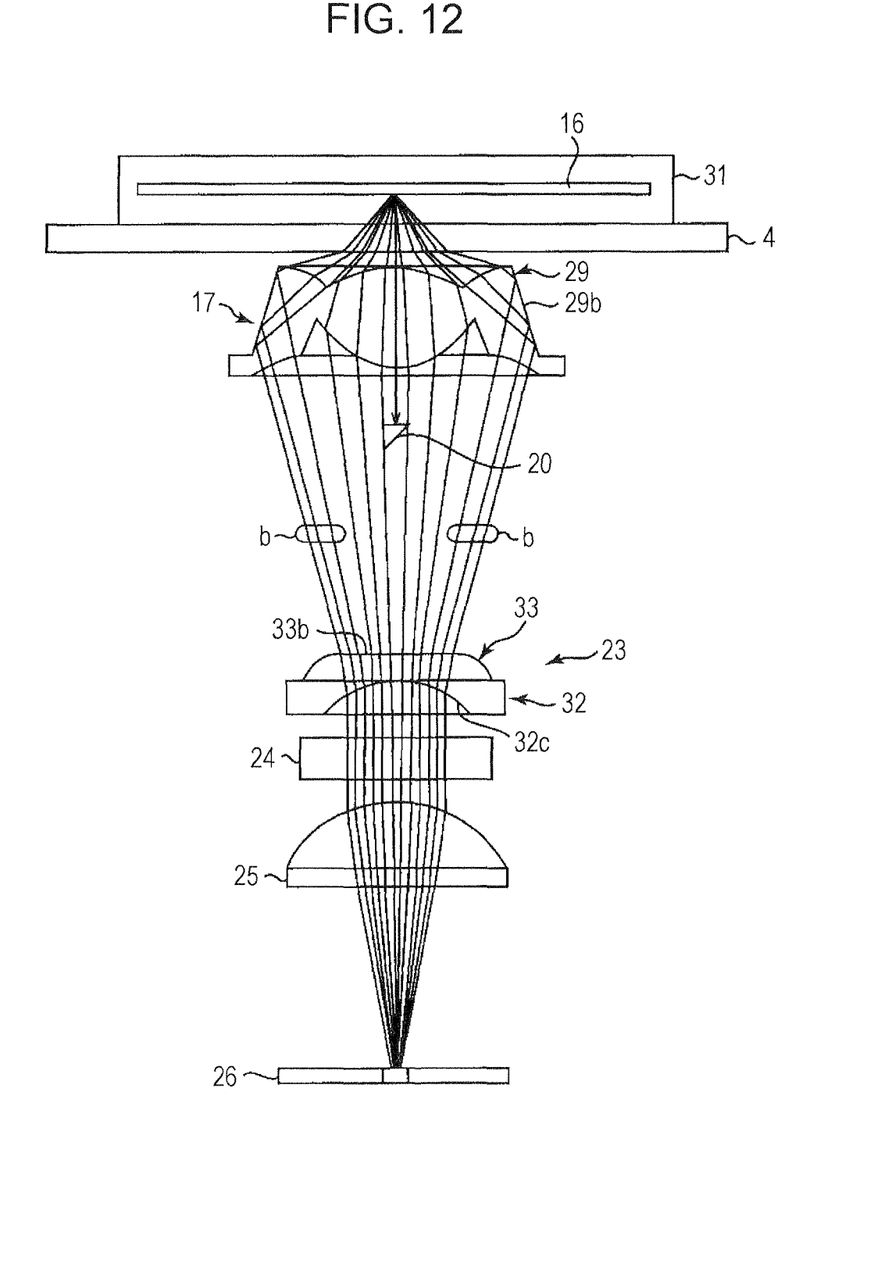
FIG. 12 is a ray diagram from the objective lens to a pinhole when the sample is sealed in the two-dimensional electrophoresis substrate in FIG. 3.

That is, first, as illustrated in FIGS. 12 and 9(b), in the "second case", the angle of the reflecting surface (side surface) 29b, the curvature of the surface through which the totally reflected light passes, and so on in the objective lens 17 and the shape of the first lens 23 are set to satisfy Condition 1 where the fluorescence component a refracted by the convex lens part 28 of the objective lens 17, of the fluorescence from the sample 16, is incident on a first region passing through an area A1 of the flat face 33h and an area B1 of the concave curved face 32c in the first lens 23 and the fluorescence component b totally reflected by the side surface 29b is incident on a second region passing through an area A2 of the flat face 33b and an area B2 of the concave curved face 32c in the first lens 23.

With this, the convex lens part 33 of the first lens 23 simply functions equivalently to a glass plate. Therefore, the rays of fluorescence components a and b incident on the flat face 33b of the convex lens part 33 while being collected are refracted to become more parallel to the optical axis, and are diverged to become more parallel to one another (the spread angle becomes closer to 0 degrees). Then, the rays of the fluorescence components a and b are made substantially parallel to the optical axis (the spread angle is substantially 0 degrees) by further passing through the concave curved face 32c of the concave lens part 32. That is, the fluorescence component b incident on the first lens 23 is diverged in total.

More specifically, when convergent light totally reflected by the cylindrical body 29 of the objective lens 17 is to be incident on the second region of the first lens 23, the inclination angle of the incident surface (A2 of the flat face 33b) with respect to the optical axis and the inclination angle of the emission surface (B2 of the concave curved face 32c) with respect to the optical axis in the second region are first set such that the convergent light is refracted into light more parallel to the optical axis. Next, to make the spread angle closer to 0 degrees, the sum of the curvature of the incident surface (A2 of the flat face 33b) and the curvature of the emission surface (B2 of the concave curved face 32c) in the second region is set such as to diverge the incident light. In this case, since the curvature of A2 of the flat face 33b is "0", the sum of curvatures is set such as to diverge the incident light by setting the curvature of B2 of the concave curved face 32c to diverge the incident light.

As a result, the fluorescence components a and b incident on the first lens 23 are converted into light nearly parallel to the optical axis by optimally setting the inclination angle and curvature of the area B1 and the inclination angle and curvature of the area B2 in the concave curved face 32c.

Figure 13:
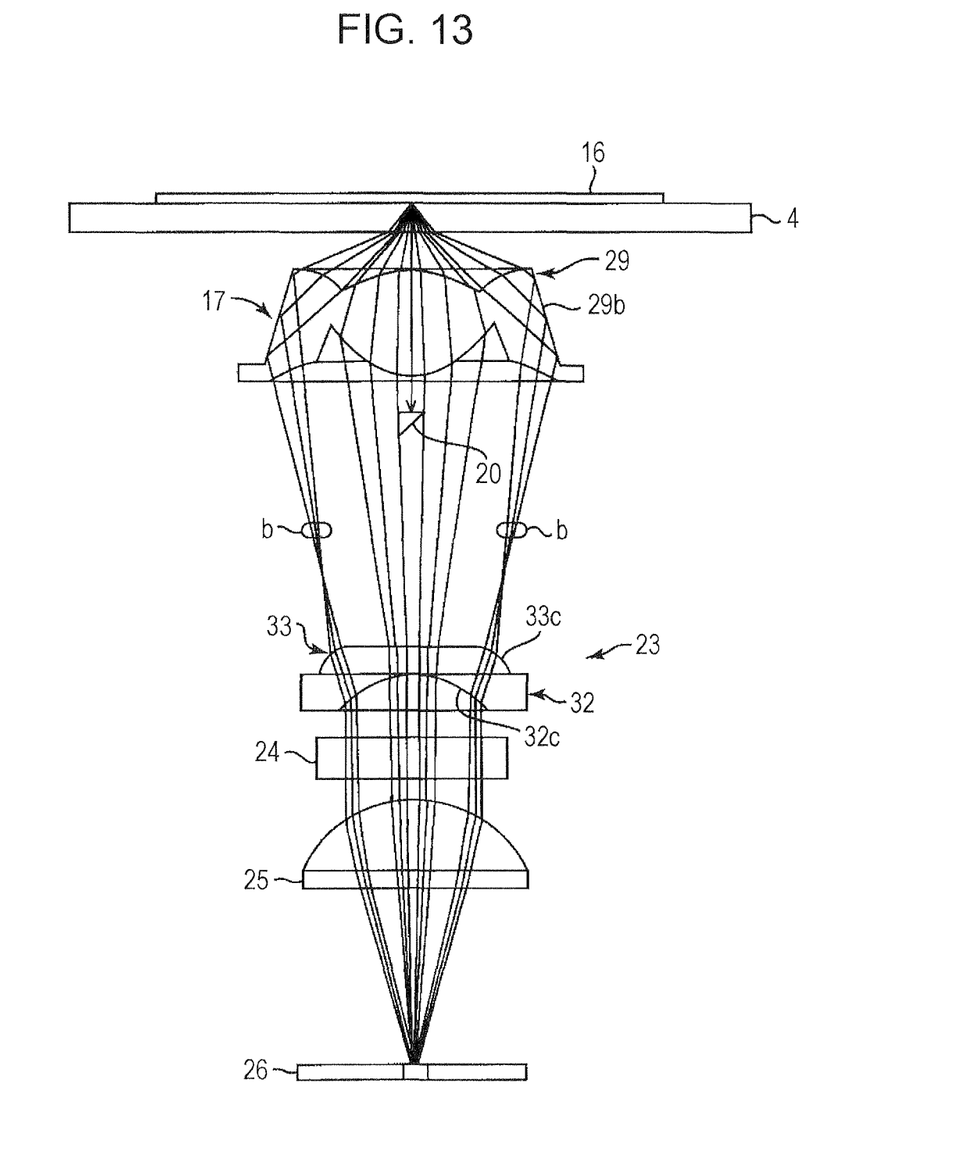
FIG. 13 is a ray diagram when the sample is directly placed in FIG. 12.

Next, as illustrated in FIGS. 13 and 9(a), in the above "first case", the angle of the reflecting surface (side surface) 29b, the curvature of the surface through which the totally reflected light passes, and so on in the objective lens 17 and the shape of the first lens 23 are set to satisfy Condition 2 where the fluorescence component b totally reflected by the side surface 29b of the objective lens 17, of the fluorescence from the sample 16, is collected and then enters a third region passing through an area A3 of the convex curved face 33c and an area B3 of the concave curved face 32c in the first lens 23.

In this case, the fluorescence component a refracted by the convex lens part 28 of the objective lens 17 is unsusceptible to the change in distance between the objective lens 17 and the sample 16. Hence, similarly to the "second case", the fluorescence component a enters the first region passing through the area A1 of the flat face 33b and the area B1 of the concave curved face 32c in the first lens 23.

With this, the convex lens part 33 of the first lens 23 functions equivalently to a convex lens. Therefore, the rays of the fluorescence component b, which enter the convex curved face 33c of the convex lens part 33 while diverging, are refracted to be more parallel to the optical axis, and are collected to be more parallel to one another (spread angle becomes closer to 0 degrees). The rays of the fluorescence component b further pass through the concave curved face 32c of the concave lens part 32, and are made substantially parallel to the optical axis (spread angle substantially becomes 0 degrees). That is, the fluorescence component b incident on the first lens 23 is collected in total.

More specifically, when divergent light diverged after being totally reflected by the cylindrical body 29 of the objective lens 17 and temporarily converged is to be incident on the third region of the first lens 23, first, the inclination angle of an incident surface (A3 of the convex curved face 33c) with respect to the optical axis and the inclination angle of an emission surface (B3 of the concave curved face 32c) with respect to the optical axis in the third region are set such as to refract the incident light into light more parallel to the optical axis. Next, to make the spread angle closer to 0 degrees, the sum of the curvature of the incident surface (A3 of the convex curved face 33c) and the curvature of the emission surface (B3 of the concave curved face 32c) in the third region is set such as to converge the incident light. In this case, the curvature of A3 of the convex curved face 33c is "curvature to converge incident light" and the curvature of B3 of the concave curved face 32c is "curvature to diverge incident light." Hence, the sum of the curvatures is set to converge the incident light by making the curvature of B3 of the concave curved face 32c less than the curvature of A3 of the convex curved face 33c.

As a result, the fluorescence component b incident on the first lens 23 is converted into light nearly parallel to the optical axis by optimally setting the inclination angle and curvature of the area A3 of the convex curved face 33c and the inclination angle and curvature of the area B3 of the concave curved face 32c.

When the curvatures of the incident surface and the emission surface in the first to third regions of the first lens 23 are set at "0", that is, when each of the regions is formed by a part of a triangular prism, the spread angle of the incident light can be improved to a certain degree by the angle formed by the incident surface and the emission surface. However, the spread angle cannot be controlled to become substantially 0 degrees. Accordingly, in this embodiment, as described above, the curvature of at least one of the incident surface and the emission surface in each region is set at a value different from "0" so that the total curvature becomes the curvature such as to converge or diverge the incident light.

As described above, in this embodiment, the angle of the reflecting surface (side surface) 29b, the curvature of the surface, through which totally reflected light passes, and so on in the objective lens 17 and the shapes, including the inclination angles and the curvatures, of the area A3 of the convex curved face 33c and the areas B1 to B3 of the concave curved face 32c in the first lens 23 are set to satisfy Conditions 1 and 2 described above. Therefore, in both the "first case" where the sample 16 is directly placed on the sample table 4 and the "second case" where the sample 16 is placed on the sample table 4 while being sealed in the two-dimensional electrophoresis substrate 31, the rays of the fluorescence component a refracted by the convex lens part 28 and the fluorescence component b totally reflected by the side surface 29b in the objective lens 17 can made nearly parallel to the optical axis when emitted from the first lens 23. Therefore, stray light can be accurately cut by the wavelength filter 24.

In order for the first lens 23 to convert light rays, which are totally reflected by the cylindrical body 29 of the objective lens 17 at different reflection angles and different spread angles between the "first case" and the "second case", into light nearly parallel to the optical axis and having a spread angle of about 0, it is necessary to simultaneously set the "inclination angle" and "curvature" of the first lens 23 at appropriate values. However, in the normal concave lens 30 having a single curved surface, as illustrated in FIGS. 6 and 7, it is significantly difficult to simultaneously set the inclination angle and the curvature at appropriate values.

Accordingly, in this embodiment, the inclination angle and curvature are simultaneously set at appropriate values by utilizing both the incident surface and the emission surface in both the second region and the third region of the first lens 23. That is, the total values of the "inclination angles" and the "curvatures" of the incident surface and the emission surface in each region are important. Accordingly, first, both the "inclination angle" and the "curvature" are set to be different between the incident surface A2 of the second region and the incident surface A3 of the third region. Secondly, both the "inclination angle" and the "curvature" are set to be different between the emission surface B2 of the second region and the emission surface 33 of the third region. With this, both the incident surface and the emission surface can be utilized in both the regions, and the degree of flexibility in design of the "inclination angle" and the "curvature" can be increased.

As described above, in this embodiment, the detection optical system composed of the first lens 23 for converting fluorescence collected by the objective lens 17 into substantially parallel light, the wavelength filter 24 for cutting excitation light, the second lens 25 for collecting the fluorescence, the pinhole 26 for cutting the stray light, and the detector 27 for detecting the fluorescence is integrally stored in the scanning module 9 that performs two-dimensional scanning in the first scanning direction and the second scanning direction.

The objective lens 17 is structured to have the convex lens part 28 in the center portion and the truncated conical cylindrical body 29 around the convex lens part 28. Therefore, the fluorescence component b having too wide an emission angle to fit in the convex lens part 28, of the fluorescence emitted from the sample 16, can be totally reflected and collected by the side surface 29b of the cylindrical body 29, and even light having too wide an emission angle to be collected by the normal convex lens can be collected. As a result, the light collection efficiency of the fluorescence can be enhanced, and the S/N ratio can be prevented from being decreased by the existence of fluorescence that is blocked by the prism 20 disposed on the optical axis of the objective lens 17, but is not detected by the detector 27. Thus, a fluorescence information reading device having high sensitivity can be realized.

Therefore, according to the embodiment, unlike the above-described conventional image information reading device, it is unnecessary to provide the concave mirror for reflecting fluorescence, which is emitted to the upper side of the sample 16, in a downward direction and to move the concave mirror in the same directions in synchronization of movement of the scanning module 9. For this reason, the scanning mechanism for two-dimensional scanning is not complicated.

Further, the size of the objective lens 17 can be made smaller than when the fluorescence component b having a wide emission angle is collected by the normal convex lens having high NA. Further, since the objective lens 17 collects fluorescence from the sample 16 and causes the fluorescence to enter the second lens 23, it is possible to also reduce the sizes of the optical elements disposed on the optical path along which the fluorescence is guided to the detector 27, such as the first lens 23, the wavelength filter 24, and the second lens 25.

By reducing the sizes of the optical elements such as the objective lens 17, the first lens 23, the wavelength filter 24, and the second lens 25, the weight of the scanning module 9 incorporating the irradiation optical system and the detection optical system can be reduced. Therefore, it is possible to simplify the structure of the scanning mechanism and to reduce the weight of the scanning mechanism so that the scanning module 9 can perform high-speed scanning. Therefore, it is possible to detect a two-dimensional fluorescence distribution at a plurality of different positions on the sample 16 at high speed.

The first lens 23 is shaped to include the concave lens part 32 with the concave curved face 32c in the center portion of the flat face 32a and the convex lens part 33 with the convex curved face 33c around the flat face 33b. The first lens 23 includes the first region, the second region, and the third region provided from the center portion toward the outer side.

Here, the first region and the second region are formed by the regions passing through the flat face 33b of the convex lens part 33 and the concave curved face 32c of the concave lens part 32, and convert incident rays into rays more parallel to the optical axis and diverge the rays in total. The third region is formed by the region passing through the convex curved face 33c of the convex lens part 33 and the concave curved face 32c of the concave lens part 32, and converts incident rays into rays more parallel to the optical and collects the rays in total.

As described with reference to FIGS. 10 and 11, since the apparent light source P'2 is located near the upper end portion of the objective lens 17, in the "second case" where the optical path 12 after total reflection by the objective lens 17 is likely to shift toward the optical axis (toward the center), the fluorescence component b totally reflected by the objective lens 17 is caused to enter the second region of the first lens 23. In this case, the second region converts the incident rays into rays more parallel to the optical axis and diverges the rays in total. For this reason, when light totally reflected by the objective lens 17 is collected, the rays of the fluorescence component b emitted from the second region of the first lens 23 are nearly parallel to one another and nearly parallel to the optical axis.

Further, in the "first case", the fluorescence component b totally reflected by the objective lens 17 is caused to enter the third region of the first lens 23. In this case, the third region converts the incident rays into rays more parallel to the optical axis and collects the rays in total. For this reason, when light totally reflected by the objective lens 17 and entering the first lens 23 is diverged, the rays of the fluorescence component b emitted from the third region of the first lens 23 become nearly parallel to one another and nearly parallel to the optical axis.

Here, to cause the light totally reflected by the objective lens 17 to enter the first lens 23 to be diverged, as illustrated in FIG. 13, the light totally reflected by the objective lens 17 is temporarily collected before entering the first lens 23.

As described above, the angle of the reflecting surface (side surface) 29b, the curvature of the surface, through which the totally reflected light passes, and so on in the first lens 23 and the shapes, including the inclination angles and the curvatures, of the convex curved face 33c and the concave curved face 32c in the first lens 23 are set so that the light totally reflected by the objective lens 17 can be collected and can enter the second region of the first lens 23 in the "second case" and so that the light totally reflected by the objective lens 17 can be diverged after being temporarily collected and can enter the third region of the first lens 23 in the "first case."

Therefore, in this embodiment, even if the distance from the objective lens 17 to the apparent light source P' is different between the case where the sample 16 is directly placed on the sample table 4 and the case where the sample 16 is placed on the sample table 4 while being sealed in the two-dimensional electrophoresis substrate 31, the fluorescence component b totally reflected by the side surface 29b of the objective lens 17 can be made nearly parallel to the optical axis when emitted from the first lens 23. Therefore, stray light can be accurately cut by the wavelength filter 24.

Further, the fluorescence component a refracted by the convex lens part 28 of the objective lens 17 and the fluorescence component b totally reflected by the side surface 29b can be collected at the position of the hole of the pinhole 26 via the first lens 23. Therefore, even when the distance from the objective lens 17 to the apparent light source P' is different, the fluorescence can be stably detected by the detector 27 in a constant light collecting state.

That is, according to this embodiment, when the fluorescence collecting efficiency is enhanced by collecting the fluorescence having too wide an emission angle to be collected by the normal convex lens, of the fluorescence emitted from the sample 16, while utilizing the objective lens 17 having the convex lens part 28 in the center portion and the truncated conical cylindrical body 29 around the convex lens part 28, even if the distance from the objective lens 17 to the apparent light source P' is different, the fluorescence can be detected accurately and stably.

As described above, in the embodiment, the first lens 23 has two regions, that is, the second region and the third region, as the regions on which the light totally reflected by the cylindrical body 29 of the objective lens 17 is to be incident. However, the present invention is not limited to two regions. Three or more regions may be provided in accordance with the number of changes in the distance between the objective lens 17 and the sample 16.

REFERENCE SIGNS LIST

1: fluorescence detection device
4: sample table
5: PC
6: scanning stage
9: scanning module
16: sample
17: objective lens
18: light source
19: lens unit
20: reflecting mirror
21: lens holder
22: driving unit
23: first lens
24: wavelength filter
25: second lens
26: pinhole
27: detector
28, 33: convex lens part
29: cylindrical body
31: two-dimensional electrophoresis substrate
32: concave lens part
32a, 32b, 33a, 33b: flat face
32c: concave curved face
33c: convex curved face.

The invention claimed is:
1. An optical unit comprising:
an objective lens element that collects light from a measuring object; and
a conversion lens that converts the light collected by the objective lens element into substantially parallel light,
wherein the objective lens element includes a total reflection part that is located in a peripheral portion to collect light by total reflection on a side surface,
wherein the conversion lens includes a plurality of regions on which the light from the total reflection part of the objective lens element is to be incident, the plurality of regions being provided in accordance with a distance between the objective lens element and the measuring object, and
wherein the conversion lens converts light from the objective lens element incident on all portions including the plurality of regions into the parallel light substantially parallel to an optical axis.
2. The optical unit according to claim 1,
wherein the light entering the plurality of regions of the conversion lens from the total reflection part of the objective lens element has different spread angles in accordance with the distance between the objective lens element and the measuring object, and wherein each of the plurality of regions of the conversion lens converts the incident light having the different spread angles into light whose spread angle is substantially 0 degrees.

3. The optical unit according to claim 2, wherein, in each of the plurality of regions of the conversion lens, the sum of a curvature of an incident surface and a curvature of an emission surface is a curvature to diverge the incident light when the spread angle of the incident light is an angle that represents convergence, and the sum of the curvature of the incident surface and the curvature of the emission surface is a curvature to converge the incident light when the spread angle of the incident light is an angle that represents divergence.

4. The optical unit according to claim 1,
wherein the objective lens element has a refraction part located in a center portion to collect light by refraction, and
wherein the conversion lens has, in a peripheral portion, the region on which the light is to be incident from the total reflection part of the objective lens element.

5. The optical unit according to claim 1,
wherein the total reflection part of the objective lens element has a concentric shape with the optical axis, and
wherein the plurality of regions of the conversion lens have concentric shapes with the optical axis.

6. The optical unit according to claim 1,
wherein the measuring object is placed on a sample table having a light transmissive property,
wherein the objective lens element and the conversion lens are disposed opposed to a surface of the sample table opposite from a surface on which the measuring object is placed, and
wherein the objective lens element collects the light emitted from the measuring object via the sample table.

7. A fluorescence detection device comprising:
a light source unit that irradiates a measuring object with excitation light that excites fluorescence;
the optical unit according to claim 1 on which the fluorescence emitted from the measuring object by the irradiation of the excitation light is to be incident, the optical unit converting the incident fluorescence into substantially parallel fluorescence;
a wavelength filter on which the substantially parallel fluorescence from the optical unit is to be incident, the wavelength filter reducing a light component with a wavelength equal to a wavelength of the excitation light; and
a photodetection element that detects the fluorescence from the wavelength filter,
wherein the objective lens element in the optical unit has, in a center portion, an excitation-light transmitting part that transmits the excitation light from the light source unit, irradiates the measuring object with the excitation light from the light source unit via the excitation-light transmitting part, and collects the fluorescence from the measuring object.

8. A fluorescence detection method comprising:
emitting, from a light source unit, excitation light that excites fluorescence;
applying the excitation light from the light source unit to a measuring object through a center portion of the objective lens element in the optical unit according to claim 1;
collecting the fluorescence emitted from the measuring object by the application of the excitation light by the objective lens element;
converting the fluorescence collected by the objective lens element into substantially parallel light by the conversion lens in the optical unit;
subtracting, by a wavelength filter, a light component having a wavelength equal to a wavelength of the excitation light from the substantially parallel fluorescence converted by the conversion lens; and
detecting the fluorescence from the wavelength filter by a photodetection element.

* * * * *